(12) United States Patent
Honda et al.

(10) Patent No.: US 8,054,940 B2
(45) Date of Patent: Nov. 8, 2011

(54) IMAGE CAPTURING SYSTEM FOR MEDICAL USE, IMAGE PROCESSING APPARATUS, AND IMAGE PROCESSING METHOD

(75) Inventors: Michitaka Honda, Takamatsu (JP); Osamu Toyama, Hino (JP)

(73) Assignees: Konica Minolta Medical & Graphics, Inc., Tokyo (JP); Institute of National Colleges of Technology, Tokyo (JP)

( * ) Notice: Subject to any disclaimer, the term of this patent is extended or adjusted under 35 U.S.C. 154(b) by 182 days.

(21) Appl. No.: 12/474,470

(22) Filed: May 29, 2009

(65) Prior Publication Data

US 2009/0296884 A1 Dec. 3, 2009

(30) Foreign Application Priority Data

May 30, 2008 (JP) ................................. 2008-143774

(51) Int. Cl.
*G01N 23/04* (2006.01)
(52) U.S. Cl. .............................. 378/62; 378/98; 382/132
(58) Field of Classification Search .................... 378/62, 378/91, 98, 98.2, 98.8, 98.9; 382/132
See application file for complete search history.

(56) References Cited

U.S. PATENT DOCUMENTS 5,665,969 A * 9/1997 Beusch ..................... 250/370.09

FOREIGN PATENT DOCUMENTS

| JP | 5-161631 A | 6/1993 |
| JP | 5-161632 A | 6/1993 |
| JP | 5-161633 A | 6/1993 |
| JP | 5-181954 A | 7/1993 |

* cited by examiner

*Primary Examiner* — Jurie Yun
(74) *Attorney, Agent, or Firm* — Brinks Hofer Gilson & Lione (57) ABSTRACT

The present invention provides a technique capable of objectively discriminating the constituent of a subject also in an image in which density difference is not easily discriminated on a gray image obtained by image capturing for medical use using X-rays. An image capturing system for medical use includes: a detecting unit for detecting an X-ray dose by absorbing X-rays passed through a subject in image capturing for medical use and outputting absorbed X-ray dose information; an obtaining unit for obtaining image information of the subject from the absorbed X-ray dose information; an image processing unit for calculating average detection energy in each first predetermined region in the image information; and an output unit for outputting the average detection energy.

15 Claims, 5 Drawing Sheets

IMAGE CAPTURING SYSTEM FOR MEDICAL USE, IMAGE PROCESSING APPARATUS, AND IMAGE PROCESSING METHOD

This application is based on application No. 2008-143774 filed in Japan, the contents of which are hereby incorporated by reference.

BACKGROUND OF THE INVENTION

1. Field of the Invention

The present invention relates to an image processing technique enabling a constituent of a subject in a captured image for medial use to be discriminated.

2. Description of the Background Art

In a radiographic image used for medical diagnosis, an image density proportional to a total amount of energy spectrum detected by a detector in a radiographic apparatus (hereinafter, referred to as "gray image") is formed. In the gray image, a pixel density $I_{kV}$ of an image obtained by collecting when a tube voltage of an X-ray tube of the radiographic apparatus is kV can be expressed as the following equation (1) using energy of X-ray (hereinafter, referred to as X-ray energy) E.

$$I_{kV} = x \int_0^{kV} EP_{kV}(E)\exp\{-\mu(E)L\}dE \qquad (1)$$

$P_{kV}(E)$ denotes the number of photons of X-ray (hereinafter, referred to as X-ray photon number) per pixel detected by the detector at X-ray energy E, $\mu(E)$ denotes a linear attenuation coefficient [cm$^{-1}$] of the subject through which the X-ray passed, and L denotes a thickness [cm] of the subject. A constant κ denotes a system gain for converting a total amount of the X-ray energy integrated by the detector of the radiographic apparatus to pixel density.

In a conventional technique, a two-dimensional distribution of $I_{kV}$ is provided for diagnosis. Based on light and shade information of an image which changes according to the linear attenuation coefficient of a substance constituting the subject, a position of a bone or an organ, a presence or absence of a lesion, and the like is diagnosed.

However, since the attenuation of an X-ray is determined by a product of the linear attenuation coefficient of the substance and the thickness of the substance as expressed by the equation (1), if the products are the same value, the densities of images are the same. In other words, when it is assumed that there are two kinds of substances A and B, if the product of the linear attenuation coefficient and the thickness of the substance A and the product of the linear attenuation coefficient and the thickness of the substance B are the same, X-rays passing through the substances A and B attenuate to a similar extent, so that the substances A and B cannot be discriminated from each other. Therefore, when the substance A is a bone and the substance B is a tumor, even if the tumor develops in a portion of the bone with a thin thickness, there is a case such that an image density of the tumor is almost equal to that of a portion of the bone around the tumor. For example, in a case such that a tumor develops fortuitously in a portion having a low bone density or a thin thickness of the bone, the image density hardly changes in a gray image, so that it is impossible to find the tumor in the gray image. Moreover, in a case of a chest X-ray diagnosis, in the diagnosis of a gray image, the density of a display image of a tumor overlapped on a diaphragm or a mediastinum is low, and the tumor cannot be represented with sufficiently high contrast. Consequently, a tumor is not easily found and is sometimes overlooked.

To address the drawback, as a first conventional technique, a technique of eliminating a shadow of a bone by a so-called energy subtraction method and forming an image of only a soft tissue is widely known. The energy subtraction method is a method of collecting two kinds of radiographic images of the same subject while changing quality of an X-ray, giving different weighting factors to images so that the attenuation of the X-rays caused by a bone become the same, and performing subtraction (refer to, for example, Japanese Patent Application Laid-Open No. 05-181954).

However, in the energy subtraction method, a beam hardening phenomenon occurs such that the linear attenuation coefficient of a bone changes apparently according to the thickness or the like. It is therefore impossible to completely eliminate a bone having various thicknesses. In addition, since a characteristic value itself of an image obtained by the energy subtraction method is meaningless, light and shade information of images is various in image capturing operations. Accordingly, only a relative evaluation in a single image can be performed.

As a second conventional technique for improving the energy subtraction method, a radiation diagnostic apparatus is proposed, which can recognize that composition substances of a subject are different from each other even if radiation absorption amounts thereof are the same by obtaining a radiation absorption coefficient of a subject when the thickness of the subject is equal to that of a reference substance, calculating a difference between the obtained radiation absorption coefficient and a radiation absorption coefficient of a reference material, and obtaining an image of the difference (refer to, for example, Japanese Patent Application Laid-Open No. 05-161632).

As a third conventional technique, a radiation diagnostic apparatus is proposed, which can recognize that composition substances of a subject are different from each other even if X-ray transmission amounts thereof are the same by obtaining a change in an X-ray transmission amount relative to a change in the energy of an X-ray in a plurality of regions pixel by pixel (refer to, for example, Japanese Patent Application Laid-Open No. 05-161631).

Further, as a fourth conventional technique, a radiation diagnostic apparatus of obtaining an average absorption coefficient of a subject from images captured with X-rays of a plurality of energies and calculating a substance existence amount pixel by pixel is proposed (refer to, for example, Japanese Patent Application Laid-Open No. 05-161633).

In the second to fourth conventional techniques, the drawback that an error easily occurs in diagnosis due to various thicknesses of a bone like in a simple energy subtraction method is improved.

However, in the second conventional technique, process is performed based on image data obtained by the energy subtraction method. An obtained value itself is meaningless, and the light and shade information of an image varies according to the image processing method. Therefore, only a relative evaluation can be made.

In the third conventional technique, only changes in a region subjected to image capture are compared. Further, in the fourth conventional technique, an existence amount of a substance per region based on the X-ray average absorption coefficient is a display target. Similar to the first conventional technique, a value itself is meaningless, obtained data varies according to the image processing methods, and only a relative evaluation can be made.

SUMMARY OF THE INVENTION

The present invention is directed to an image capturing system for medical use.

According to the present invention, the image capturing system for medical use includes: a detecting unit for detecting an X-ray dose by absorbing X-rays passed through a subject in image capturing for medical use and outputting absorbed X-ray dose information; an obtaining unit for obtaining image information of the subject from the absorbed X-ray dose information; an image processing unit for calculating average detection energy in each first predetermined region in the image information; and an output unit for outputting the average detection energy.

With this configuration, by calculating a value of average detection energy as a physical quantity having clear meaning and displaying the value together with a gray image, a constituent of a subject with respect to a shadow in which density difference is not easily discriminated on the gray image can be discriminated.

The present invention is also directed to an image processing apparatus.

According to the present invention, the image processing apparatus includes: an image processing unit for calculating average detection energy in each first predetermined region in image information obtained by image capturing for medical use performed by an image capturing apparatus for medical use by estimating the number of photons of X-rays absorbed by a detecting unit of the image capturing apparatus for medical use from the image information; and an output unit for outputting the average detection energy.

With this configuration, by calculating a value of average detection energy as a physical quantity having clear meaning and displaying the value together with a gray image, a constituent of a subject with respect to a shadow in which density difference is not easily discriminated on the gray image can be discriminated. Further, at the time of calculating the value of the average detection energy, by estimating from the image information the number of X-ray photons which are not easily detected successively due to variations in the energy of applied X-rays, the number of X-ray photons can be easily and properly obtained.

The present invention is also directed to an image capturing method.

Therefore, an object of the present invention is to provide a technique capable of objectively discriminating the constituent of a subject also in an image in which density difference is not easily discriminated on a gray image obtained by image capturing for medical use using X-rays.

These and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the present invention will be described below with reference to the drawings.

<General Configuration of Image Capturing System for Medical Use>

Figure 1:
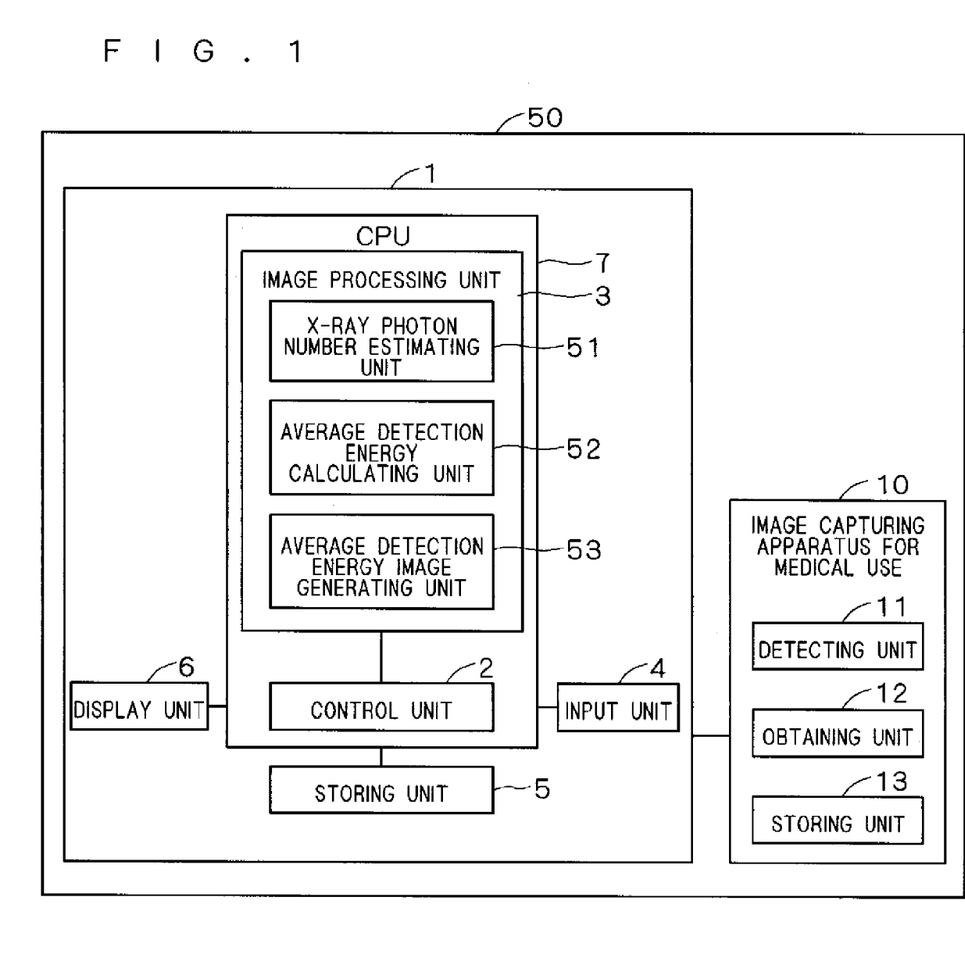
FIG. 1 is a block diagram showing a configuration common to embodiments applied to an image capturing system 50 for medical use.

FIG. 1 is a block diagram showing a configuration common to embodiments of applying the present invention to an image capturing system 50 for medical use which can process a diagnostic image of a specific region (for example, a lung) of a patient.

The image capturing system 50 for medical use includes an image processing apparatus 1 and an image capturing apparatus 10 for medical use. In first to fourth embodiments, a radiographic apparatus is used as the image capturing apparatus 10 for medical use.

As shown in FIG. 1, in the image processing apparatus 1, a control unit 2, an image processing unit 3, an input unit 4, a storing unit 5, a display unit 6, and a CPU 7 are connected.

The CPU 7 includes the control unit 2 and the image processing unit 3.

The control unit 2 as control means executes a control program stored in the storing unit 5 described below to thereby determine operations of the entire image processing apparatus 1, give an instruction to the entire image processing apparatus 1, and also give an instruction to the display unit 6 described below.

The image processing unit 3 as image processing means is configured by, for example, a CPU, works as means for realizing each function, and generates an average detection energy image. The image processing unit 3 includes an X-ray photon number estimating unit 51, an average detection energy calculating unit 52, and an average detection energy image generating unit 53. Using image information inputted to the input unit 4, the X-ray photon number estimating unit 51 estimates an average number of X-ray photons absorbed by a detecting unit 11 of the image capturing apparatus 10 for medical use. The average number of X-ray photons is an average of the numbers of photons in energy distributions of X-rays. The average detection energy calculating unit 52 calculates average detection energy in each of first predetermined area in the image information. The average detection energy is obtained by dividing an image density of an image by a product between a system gain and the average number of X-ray photons. The average detection energy image generating unit 53 generates an average detection energy image based on the average detection energy calculated by the average detection energy calculating unit 52.

The input unit 4 inputs image information and a system parameter as a parameter of the image capturing apparatus 10 for medical use described below. The image information is inputted from the image capturing apparatus 10 for medical use connected to the image processing apparatus 1.

The storing unit 5 is configured by a storage device such as a semiconductor memory or a hard disk and stores information such as a program executed by the control unit 2, information necessary to execute the program, and an image inputted from the input unit 4.

The display unit 6 as output means is configured by, for example, a liquid crystal display or the like and visibly outputs an average detection energy image or the like generated by the image processing unit 3.

The image capturing apparatus 10 for medical use includes the detecting unit 11 as detecting means, an obtaining unit 12 as obtaining means, and a storing unit 13. The image capturing apparatus 10 for medical use captures an image of a predetermined region included in an internal organ or the like of a person subjected to image capturing. The image capturing apparatus 10 performs image capturing by emitting an X-ray from an X-ray generation source to the person subjected to image capturing. The detecting unit 11 detects an X-ray dose by absorbing X-rays passed through a subject in X-ray image capturing, and outputs the information (absorbed X-ray dose information). The obtaining unit 12 obtains the image information of the subject from the absorbed X-ray dose information outputted from the detecting unit 11. The storing unit 13 stores the image information. The image information stored in the storing unit 13 is transferred to the input unit 4 as necessary.

First Embodiment

The present invention gives means for providing, in addition to a conventional gray image, subject information other than a gray image by calculating an average value of X-ray energy per pixel detected by a detector, that is, average detection energy, and forming an image of a distribution of the value.

In a first embodiment, the X-ray photon number estimating unit 51 estimates an average number of X-ray photons per pixel absorbed by the detecting unit 11 by using image information obtained by performing X-ray image capturing using X-rays in a plurality of energy regions and applied X-ray dose information as information of dose of X-rays to be applied such as a tube voltage.

The average detection energy is formulated as follows.

$$\overline{M}_{kV} = I_{kV} / (x \tilde{P}_{kV}) \quad (2)$$

$$\tilde{P}_{kV} = \int_0^{kV} P_{kV}(E) \exp\{-\mu(E)L\} dE \quad (3)$$

where $\overline{M}_{kV}$ and $\tilde{P}_{kV}$ denote average detection energy per pixel at a tube voltage kV and an average number of X-ray photons, respectively.

In a case where a substance constituting a subject absorbs X-rays having lower energy than X-rays having relatively high energy, the average detection energy has a high value. For example, representative substances constituting a human body are water and bones (calcium). Since calcium has a relatively stronger physical property such that it absorbs the X-ray having lower energy than the X-ray having high energy in comparison with water, the average detection energy of the X-rays that passed through a bone has a value higher than that of water. Therefore, even if the average number $\tilde{P}_{kV}$ of X-ray photons per pixel that passed through a bone and that passed through water are the same, after passing through the bone, the number of components of relatively high energy is larger as compared with a distribution of energy of the X-ray passed through water. Consequently, in the above-described equation (1), the X-ray that passed through a bone has more components of $P_{kV}(E)$ having a large value of the energy E and fewer components having a small value of the energy E. As a result, the value of $I_{kV}$ becomes larger, and the average detection energy $M_{kV}$ calculated by the equation (2) becomes larger.

An image expressed by the equation (1) is the same X-ray image as the conventional gray image. However, the average number of X-ray photons per pixel given by the equation (3) is necessary for estimating the average detection energy.

Figure 2:
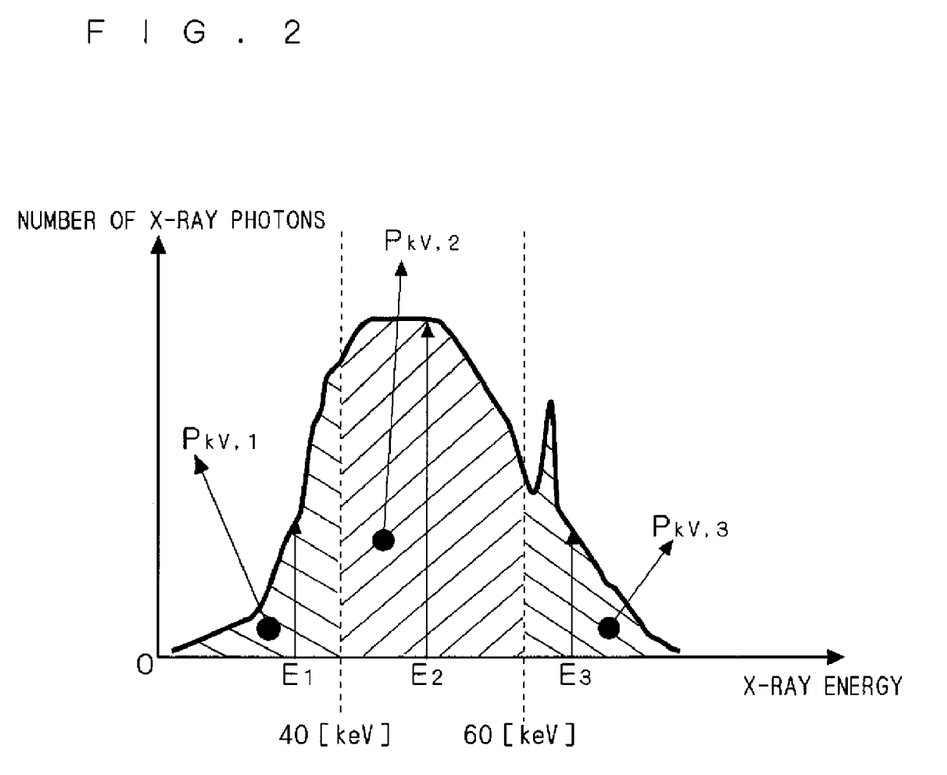
FIG. 2 is a graph showing a relation between the number of X-ray photons and X-ray energy.

FIG. 2 is a graph showing a relation between the number of X-ray photons and X-ray energy. A vertical axis of the graph shows the number of X-ray photons, and a horizontal axis of the graph shows the X-ray energy [keV]. The equations (1) and (2) express the X-ray energy successively. In the following equations, the energy range from 0 to kV [keV] is divided into three energy regions as shown in FIG. 2 and described approximately.

$$I_{kV} = n\{E_1 P_{kV,1} X_1 + E_2 P_{kV,2} X_2 + E_3 P_{kV,3} X_3\} \quad (4)$$

$$P_{kV} = P_{kV,1} X_1 + P_{kV,2} X_2 + P_{kV,3} X_3 \quad (5)$$

Where "n" denotes a number of a divided energy region. $X_n$ (n=1, 2, 3) denotes an attenuation rate of a subject and is expressed as $X_n = \exp\{-\mu(E_n)L\}$. $E_n$ and $P_{kV,n}$ (n=1, 2, 3) express representative energy of the divided three energy regions and the number of X-ray photons per pixel, respectively.

With respect to the energy regions and representative energies, a representative subject is prepared and a preliminary test is executed. By setting energy regions and values of representative energies $E_1$, $E_2$, and $E_3$ so that an influence of an approximation error between the actual image density obtained and the image density calculated by using equation (4) becomes the smallest, estimation precision of the average detection energy can be increased. The representative subject used in the preliminary test is constituted by a substance whose linear attenuation coefficient is clear. Image capturing using X-rays of the same tube voltage is performed on a substance of the number of divisions of the energy regions or larger. For example, with respect to a substance whose linear attenuation coefficient is clear, the energy regions and values of representative energies $E_1$, $E_2$, and $E_3$ may be set so that a difference between the average detection energy obtained by using the equations (1) and (3) and the average detection energy obtained by using the equations (4) and (5), that is, the influence of an approximation error is reduced. Specifically, the distribution $P_{kV}(E)$ of the number of X-ray photons per pixel outputted from an X-ray generator is measured by a spectrometer and the like in advance. Then, the energy regions and the values of representative energies $E_1$, $E_2$, and $E_3$ are determined so as to minimize the error between the value of the average detection energy obtained by using a continuous spectrum of an X-ray detected, that is, the results obtained by using the equations (1) and (3) and the value of the average detection energy obtained by setting the divided energy regions and the values of the representative energies of the present embodiment, that is, the results obtained by the equations (4) and (5). In other words, it is sufficient to obtain $\epsilon^2$ expressed by the following equation (6) while variously setting the ranges of the energy regions and variously changing the values of the representative energies $E_1$, $E_2$, and $E_3$ and use the energy ranges and the values of $E_1$, $E_2$, and $E_3$ that give the minimum $\epsilon^2$.

$$\epsilon^2 = \{[\text{average detection energies obtained by using the equations (1) and (3)}] - [\text{average detection energies obtained by using the equations (4) and (5)}]\}^2 \quad (6)$$

By using the value obtained as described above, the average detection energy can be estimated while minimizing the influence of the approximation error. Although it has been described that measurement is performed with a spectrometer at the time of obtaining $P_{kV,n}$ (n=1, 2, 3), since measurement values of a distribution of the numbers of X-ray photons outputted from the X-ray generator are already announced as known materials, setting $P_{kV,n}$ (n=1, 2, 3) can be performed based on the known materials without performing actual measurement.

In an example of dividing the X-ray energy region to three ranges of 0 to 40 [keV], 40 to 60 [keV], and 60 [keV] or larger, $E_1$ expresses energy representing the range of 0 to 40 [keV] so that $E_1=30$ [keV] can be set. Similarly, $E_2=50$ [keV], $E_3=70$ [keV], and the like can be set. On the other hand, $P_{kv,1}$ denotes the number of X-ray photons per pixel in a case where the X-ray energy is included in the range of 0 to 40 [keV]. Since it is an amount detected by the detector in a state where a subject is not placed, it can be measured in advance at the time of shipping of the system or the like. As an example, there is a method of measuring the number of X-ray photons which are incident on the region of one pixel by a measuring device such as a spectrometer in a position apart by 100 cm per tube current time product 1 mAs at various tube voltages kV. By performing the measurement at the time of shipping and storing the data in the storing unit 5, measurement values from 0 to 40 [keV] are multiplied with the detection rate of the detector and the resultant values are totaled. By correcting the value of the tube current time product set in actual image collection and the distance between the X-ray generator and the detector, $P_{kV,1}$ is obtained. Similarly, the values of $P_{kV,2}$ and $P_{kV,3}$ can also be determined. As used herein, the detection rate refers to proportion of energy detected in applied energy.

By means as described above, $E_1$, $E_2$, and $E_3$ and $P_{kV,1}$, $P_{kV,2}$, and $P_{kV,3}$ in the equations (4) and (5) are determined in advance, and image collection is executed. The present embodiment is characterized in that, at the time of the image collection, three kinds of image information are collected using three kinds of tube voltages, and attenuation rates $X_1$, $X_2$, and $X_3$ of a subject in the energy regions are obtained. For example, when the three kinds of tube voltages are set to 60, 80, and 100 [kV], the equation (4) is expressed as follows.

$$\begin{cases} I_{60} = x\{E_1 P_{60,1} X_1 + E_2 P_{60,2} X_2 + E_3 P_{60,3} X_3\} \\ I_{80} = x\{E_1 P_{80,1} X_1 + E_2 P_{80,2} X_2 + E_3 P_{80,3} X_3\} \\ I_{100} = x\{E_1 P_{100,1} X_1 + E_2 P_{100,2} X_2 + E_3 P_{100,3} X_3\} \end{cases} \quad (7)$$

Consequently, it is sufficient to solve the equation with respect to $X_1$, $X_2$, and $X_3$ on the pixel unit basis using the predetermined $E_1$, $E_2$, and $E_3$ and $P_{kV,1}$, $P_{kV,2}$, and $P_{kV,3}$ (kV=60, 80, 100) and the collected image densities $I_{60}$, $I_{80}$, and $I_{100}$. When the solution is obtained, for example, the average number $\tilde{P}_{100}$ of X-ray photons at a tube voltage 100 kV can be estimated from the equation (5). The average detection energy $\hat{M}_{100}$ can also be obtained from the equation (2).

The X-ray photon number estimating unit 51 executes the processes until the average number of X-ray photons is estimated by using the equation (5) on each pixel.

The average detection energy calculating unit 52 executes the process expressed by the equation (2) on each pixel to calculate the average detection energy.

Based on the average detection energy on each pixel calculated by the average detection energy calculating unit 52, the average detection energy image generating unit 53 generates an average detection energy image by expressing the average detection energy in a planar distribution.

Figure 3A:
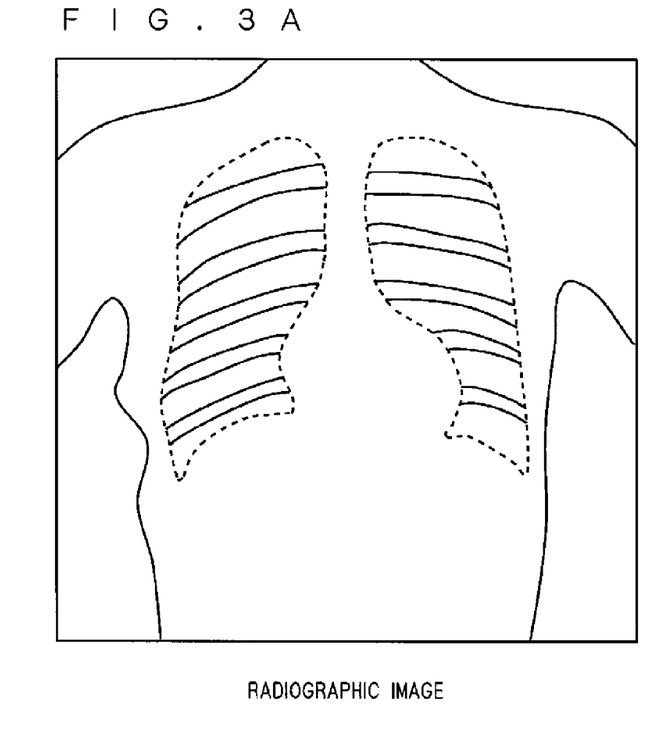
FIGS. 3A and 3B are diagrams showing an example of a display unit 6 displaying an average detection energy image and a gray image side by side.
Figure 3B:
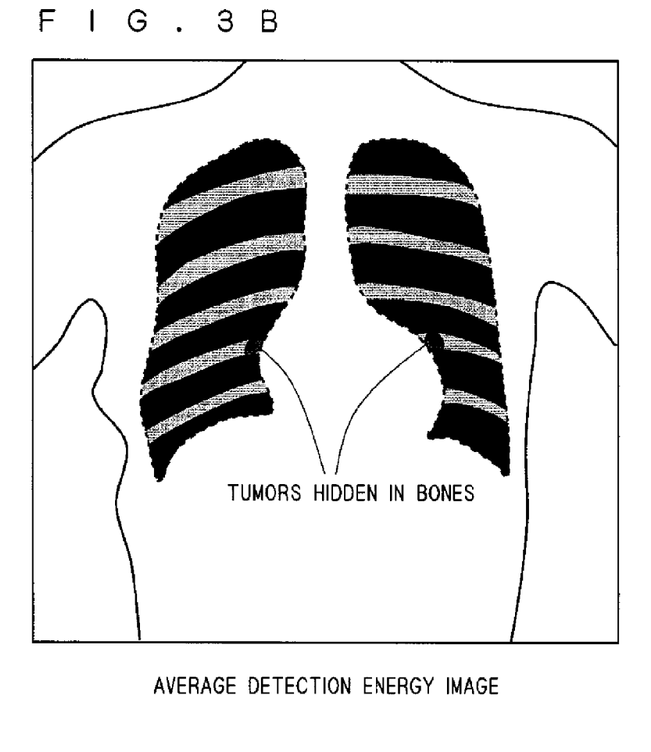

The generated average detection energy image is displayed by the display unit 6 by using a method of displaying the image and a gray image side by side, a method of displaying the image while being switched with a gray image by an operation button, a method of coloring an image in accordance with the value of the average detection energy and displaying the image so as to be overlapped on a gray image, or the like. In the case of coloring the image in accordance with the value of the average detection energy and generating the average detection energy image, for example, a predetermined reference value is set for the value of the average detection energy. A color to be displayed according to the value of the average detection energy may be set in such a manner that, when the value of the average detection energy is lower than the reference value, red is displayed, and when the value is higher than the reference value, blue is displayed. FIGS. 3A and 3B are diagrams showing an example of displaying the average detection energy image and the gray image side by side in the display unit 6. FIG. 3A shows a radiographic image as a gray image, and FIG. 3B shows an average detection energy image.

For example, a smoothing filter is applied for image information. Thereafter, by performing the process of the present embodiment, an electronic noise occurring on an image and a noise caused by variations in the number of X-ray photons may be reduced to improve estimation precision.

As described above, in the image capturing system 50 for medical use of the first embodiment, by calculating the value of the average detection energy as a physical amount having clear meaning and displaying the value together with a gray image, the constituent of a subject with respect to a shadow in which a density difference is not easily discriminated on the gray image can be discriminated. At the time of calculating the value of the average detection energy, the average number of X-ray photons from which it is difficult to successively detect variations in the energy of applied X-rays is estimated by using the image information and the applied X-ray dose information, thereby enabling the value of the average detection energy to be easily and properly obtained.

There are at least the following two specific effects in diagnose produced by obtaining the average detection energy and providing the distribution of the energy as image information.

(1) By enabling a bone or a calcified tissue containing a relatively large amount of calcium and an organ or a tumor containing a relatively large amount of water to be discriminated from each other, the tumor overlook ratio in diagnose can be lowered. For example, in a case such that a tumor develops fortuitously in a portion having a low bone density or a thin thickness of the bone, the image density hardly changes in a gray image, and there is a possibility that a presence of the tumor is overlooked. However, when the value of the average detection energy is lower than a periphery thereof, it can be known that the bone density in the region is low or the bone is thin. Therefore, the presence of a tumor can be assumed.

(2) In a case of a chest X-ray diagnosis, in the diagnosis of a gray image, the density of a display image of a tumor overlapped on a diaphragm or a mediastinum is low, and the tumor cannot be expressed with sufficiently high contrast. Consequently, a tumor is not easily found and is sometimes overlooked. In such a case, if there is a difference in the average detection energy, it shows the possibility of the presence of a tumor. Therefore, the overlook ratio of the tumor can be lowered.

Second Embodiment

In the first embodiment the X-ray energy region is divided into three regions. In a second embodiment, the X-ray energy region is divided into two regions. In the present embodiment, it is sufficient to use two kinds of tube voltages at the time of performing X-ray image capturing. For example, an average detection energy image can be generated by using two kinds of tube voltages of 60 kV and 100 kV. In the present embodiment, an approximation error between the value of the average detection energy obtained by using a continuous spectrum of an X-ray detected by the detector, that is, the results obtained by using the equations (1) and (3) and the value of the average detection energy obtained by setting the divided energy regions and the values of the representative energies of the present embodiment, that is, the results obtained by the equations (4) and (5) is larger as compared with that of the first embodiment. However, since it is sufficient to perform the X-ray image capturing only twice, the image capturing can be performed in a short period of time so that the dose of X-ray applied to a human can be reduced.

Third Embodiment

In the first and second embodiments, the image processing unit 3 estimates the average number of X-ray photons per pixel by using image information and applied X-ray dose information, thereby calculating the average detection energy per pixel. In contrast, in a third embodiment, the image processing unit 3 obtains the average detection energy by estimating the average number of X-ray photons per pixel by using average image density information in each of local areas in a radiographic image at a single tube voltage and variance information of image density in this radiographic image at this single tube voltage.

The average number of X-ray photons is a statistic amount according to Poisson distribution, and it is known that the average number of X-ray photons detected per pixel in the detecting unit 11 and the variance are equal to each other. That is, in the equations (3) and (5), the average number $\tilde{P}_{kV}$ of X-ray photons per pixel is a statistic amount, and has variations given by variance $\tilde{P}_{kV}$ as the same value around the average value. The variance is expressed as a noise in an image density on an image. In the present embodiment, a noise in an image area to obtain the average detection energy as shown in FIGS. 3A and 3B, that is, variance of the image density is measured and the average number of X-ray photons is estimated, thereby calculating the average detection energy. Specifically, a local area of N×N pixels is provided, and variance $V_{kV}^I$ of image density in the area is measured.

Figure 4A:
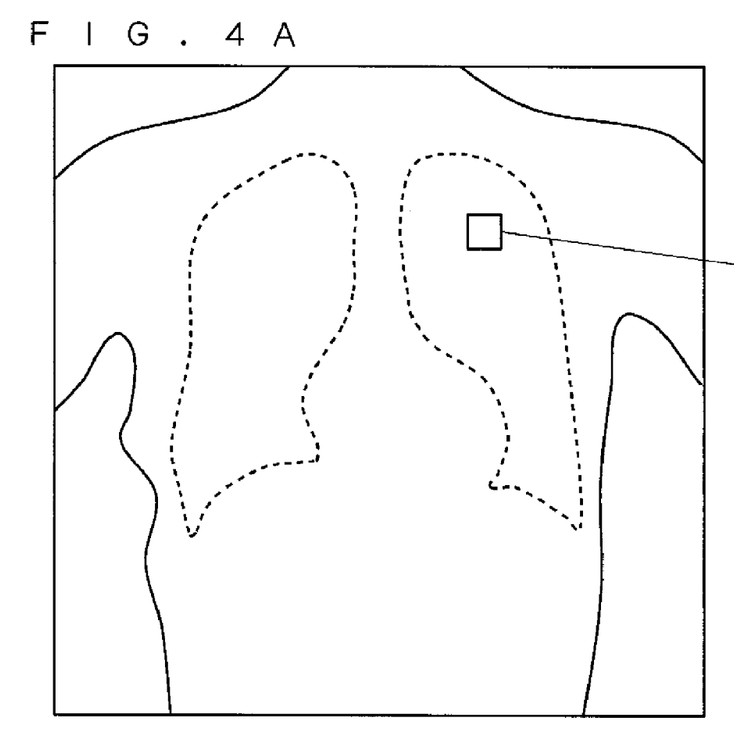
FIGS. 4A and 4B are diagrams for describing a local area of N×N pixels.
Figure 4B:
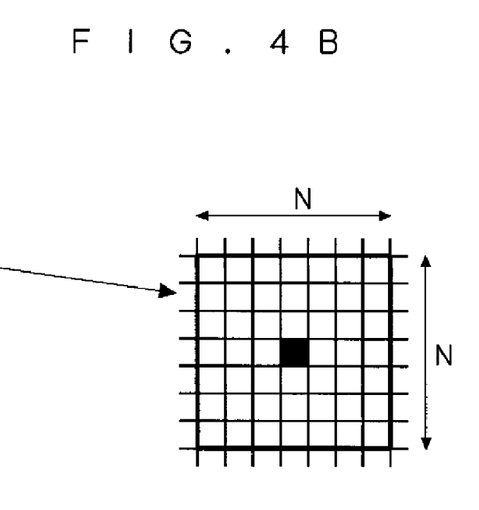

FIGS. 4A and 4B are diagrams illustrating a local area of N×N pixels. As shown in FIGS. 4A and 4B, when it is assumed that a local area of N×N pixels is provided around a pixel whose average detection energy is to be detected and the X-ray energy E given to the local region is constant, the average number of X-ray photons can be approximately obtained by the following equation (8). N is set, for example, in a range of 10 to 20.

$$\text{Average number } \tilde{P}_{kV} \text{ of X-ray photons} = \frac{I_{kV}^2}{V_{kV}^I} \quad (8)$$

$I_{kV}$: average pixel density of N×N pixels
$V_{kV}^I$: variance of pixel density in local area The reason why the average number of X-ray photons can be approximately obtained by the equation (8) will be described below.

When the X-ray energy E is constant, the image density variance of the local area can be broken down as follows.

$$V_{kV}^I = V_{kV}^P \cdot E^2 \quad (9)$$

$V_{kV}^P$: variance of the number of photons
When the number of X-ray photons is according to the Poisson distribution, from $$V_{kV}^P = \tilde{P}_{kV} \quad (10)$$

the following equation is obtained.

$$V_{kV}^I = \tilde{P}_{kV} \cdot E^2 \quad (11)$$

On the other hands the average image density is expressed as $$I_{kV} = E \cdot \tilde{P}_{kV} \quad (12)$$

the following equation is obtained.

$$\frac{I_{kV}^2}{V_{kV}} = \frac{(E \cdot \tilde{P}_{kV})^2}{\tilde{P}_{kV} \cdot E^2} = \tilde{P}_{kV} \quad (13)$$

Depending on a detector, a blur may occur due to an influence of internal light scattering or the like. There is a case that, due to the blur, a noise, that is, variance of image density is smoothed. In such a case, it is sufficient to measure in advance the degree of smoothing, obtain a smoothing coefficient β (0.0 to 1.0), and perform correction of an amount of change caused by the smoothing as shown by the following equation (14).

$$\tilde{P}_{kV} = \beta \frac{I_{kV}^2}{V_{kV}^I} \quad (14)$$

In accordance with the third embodiment, by estimating the average number of X-ray photons from which it is difficult to successively detect variations in the energy of applied X-rays by using the average image density information and the variance information of image density, the value of the average detection energy can be easily and properly obtained.

Fourth Embodiment

Figure 5A:
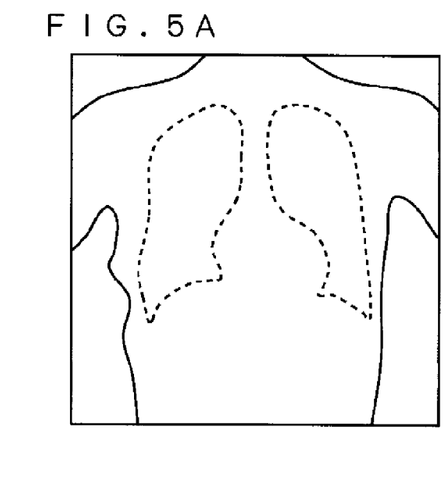
FIGS. 5A to 5C are diagrams showing a temporal subtraction.
Figure 5B:
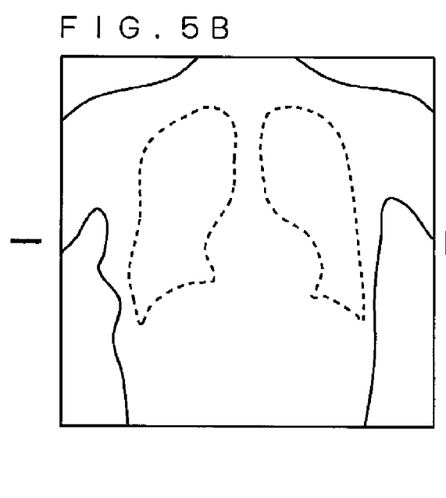
Figure 5C:
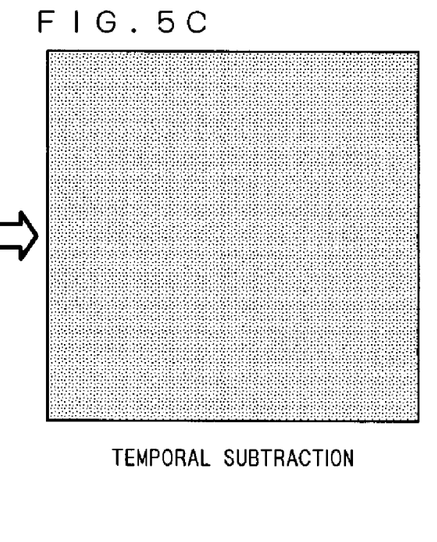

In a fourth embodiment, to improve precision of variance measurement of image density in the third embodiment, a background density of a radiographic image is eliminated. The measurement precision of variance in a local area deteriorates substantially in a case where the background density in the local area is uneven. In the present embodiment, therefore, two images are successively obtained at the same tube voltage, subtraction is performed between the two images to generate a temporal subtraction, and the background density is set to 0. FIG. 5C shows a temporal subtraction. From images shown in FIGS. 5A and 5B that are successively captured (successively captured images), the temporal subtraction (FIG. 5C) whose background density is set to 0 is generated.

By measuring variance of image density in the temporal subtraction, unevenness of the background density in a local area is eliminated, so that the measurement precision improves.

However, variance of noise measured on the temporal subtraction becomes twice due to general property of variance as expressed by the following equations (15) and (16).

$$V[I^1-I^2]=V[I^1]+V[-I^2]=V[I^1]+[I^2] \quad (15)$$

When $$V[I^1]=V[I^2]$$

$$V[I^1-I^2]=2V[I^1] \quad (16)$$

Therefore, the total number of average X-ray photons per pixel is set to a value obtained by halving the variance of the image density derived by the above measurement.

In the present embodiment, by using a sum of two successively captured images, or an average image as a gray image displayed in addition to an image showing the distribution of average energies, an S/N ratio improves more than a case of employing one of the images.

<Modifications>

Although the embodiments of the present invention have been described above, the present invention is not limited thereto.

Although the energy region is divided into two or three regions and average detection energy is calculated in the foregoing embodiment, the number of kinds of tube voltages in X-ray image capturing can also be increased to four or more. By increasing the number of kinds of the tube voltage to four or more, an approximation error between the value of the average detection energy obtained by using a continuous spectrum of an X-ray detected and the value of the average detection energy obtained by setting the divided energy regions and the values of the representative energies can be reduced.

In the foregoing embodiments, by changing the three kinds of tube voltages, the energy region is divided and the average detection energy is calculated. However, the invention is not limited thereto. For example, by changing the X-ray energy to be given to the subject while switching members which can change the distribution of an X-ray energy spectrum such as an addition filter or the like between the subject and the X-ray generator, the energy region is divided and the average detection energy may be calculated.

For example, three images are captured by disposing, in place of the three kinds of tube voltages, an aluminum plate having a thickness of 1 mm for a first image, a copper plate having a thickness of 0.5 mm for a second image, and a tantalum plate having a thickness of 0.3 mm for a third image between the subject and the X-ray generator and performing X-ray image capturing. The three captured images are subjected to a process similar to that of the first embodiment to estimate an average number of X-ray photons per pixel and calculate the average detection energy. Note that the materials and thicknesses of the added filters are not limited thereto. As long as a sufficient change occurs in the distribution of the energy spectrum of an X-ray that passed, any combination may be employed.

Although a still image has been described in the foregoing embodiments, the average number of X-ray photons may be obtained from a perspective image as a moving image. By using a perspective image, a number of images can be obtained successively. Therefore, by measuring variance of image density of an obtained image, precision of estimating the average number of X-ray photons can be improved.

For example, when the value of the tube current time product of a still image is "r" times as large as that of the perspective image, by increasing the variance of density of the perspective image by "r" times to have the same system gain κ as that of the still image, an estimation value of the variance of the still image under the same image capturing conditions can be obtained. In addition, by averaging the estimation value of the variance obtained with respect to a plurality of perspective images, an error included in the estimation value of the variance can be reduced, and the estimation precision of the average number of X-ray photons can be improved.

Further, in the third embodiment, the variance of the image density is measured in the local area of N×N pixels. In the present modification in which a number of perspective images can be used, the number of samples becomes large, and precision improves. When a size of the local area is decreased, the precision deteriorates. However, in the third embodiment, the size of the local area can be reduced, so that a spatial resolution of the average detection energy can also be improved. In particular, in a case where a sufficiently large number of perspective images are collected and the measurement precision of variance is sufficiently increased by performing averaging on these multiple images, the local area can be reduced almost to one pixel. Therefore, average detection energy of a very fine substance can also be estimated.

In the foregoing embodiments, an X-ray image is captured in the image processing apparatus 1 and variance of image density is obtained. However, the invention is not limited thereto. For example, by mounting a hardware engine capable of measuring variance of image density at speed higher than that of collecting images on the image capturing apparatus 10 for medical use, without capturing X-ray perspective views in the image processing apparatus 1, variance of the image density can be measured in real time.

Moreover, with respect to the X-ray perspective image, by eliminating the background density in a manner similar to that in an X-ray still image, the precision of variance measurement of the image density may be improved. For example, when the numbers of perspective images are set as #1, #2, . . . , and #N, first, temporal subtractions of #1–#2, #3–#4, . . . , and #(N–1)–#N are formed. In a case where the value of the tube current time product of a still image is "r" times as large as that of the perspective image in a manner similar to the above, the variance of density of the perspective image has to be increased by "r" times to have the same system gain κ as that of the still image. An average value of (N/2) pieces of variance measured on the temporal subtraction is multiplied by 0.5 r, and the resultant value is used as the estimation value of the average number of X-ray photons.

In the foregoing embodiments, the average detection energy per pixel is calculated. Alternatively, the average detection energy per area made of a plurality of pixels may be calculated.

Although the average number of X-ray photons is estimated by the equation (5) in the first embodiment, the average detection energy per pixel may be calculated without using the method of estimating the average number of X-ray photons. For example, by defining a parameter of a representative energy $E_i$, $\alpha_i = P_{kV,i} \times X_i$ and performing weighted averaging on the representative energy $E_i$ using the parameter $\alpha_i$ as a weight, the average detection energy may be calculated.

In the first to fourth embodiments, the image capturing system for medical use having the radiographic apparatus has been described. Alternatively, an image processing apparatus capable of processing a diagnostic image of a specific region (such as a lung) in a patient obtained by the image capturing apparatus for medical use may be employed.

In this case, image information may be received online from the image capturing apparatus 10 for medical use. Further, the image information can be received by reading information from a portable storing medium such as a DVD or reading information with a scanner. It is also possible to store an image of a person subjected to image capturing in a file server or the like connected via a network, and retrieve and read the image data of the corresponding person subjected to image capturing from a plurality of pieces of stored image data.

The present invention is not limited to a configuration in which the image processing apparatus is independent of the image capturing apparatus for medical use. Alternatively, a configuration of realizing means of the image processing apparatus by a computer provided in the image capturing apparatus for medical use may also be employed.

While the invention has been shown and described in detail, the foregoing description is in all aspects illustrative and not restrictive. It is therefore understood that numerous modifications and variations can be devised without departing from the scope of the invention.

What is claimed is:

1. An image capturing system for medical use, comprising:
   a detecting unit for detecting an X-ray dose by absorbing X-rays passed through a subject in image capturing for medical use and outputting absorbed X-ray dose information;
   an obtaining unit for obtaining image information of said subject from said absorbed X-ray dose information;
   an image processing unit for calculating average detection energy in each first predetermined region in said image information, wherein said image processing unit estimates a number of photons of X-rays absorbed by said detecting unit using said image information to calculate said average detection energy in each said first predetermined region in said image information, and wherein said image information includes a plurality of pieces of image information obtained by performing image capturing for medical use using X-rays in energy regions, and said image processing unit estimates the number of photons of X-rays by using said plurality of pieces of image information and applied X-ray dose information as information of dose of X-rays outputted from an X-ray generator; and
   an output unit for outputting said average detection energy.

2. The image capturing system for medical use according to claim 1, wherein said applied X-ray dose information includes values of representative energies in said energy regions and the number of photons of X-rays corresponding to said first predetermined regions in said energy regions.

3. The image capturing system for medical use according to claim 2, further comprising a storing unit for storing values of representative energies in said energy regions, wherein a value of representative energy in each of said energy regions is set in advance based on comparison between a first average detection energy and a second average detection energy, said first average detection energy is an average detection energy related to a predetermined substance obtained based on a distribution of the number of photons of X-rays outputted from said X-ray generator, and said second average detection energy is an average detection energy related to said predetermined substance obtained based on the number of photons of X-rays in each of said energy regions and candidate values of representative energies in said energy regions.

4. The image capturing system for medical use according to claim 2, further comprising a storing unit for storing a preliminary measurement value of the number of photons corresponding to each of said first predetermined regions of X-rays outputted from said X-ray generator which is set for each tube voltage of said X-ray generator, wherein the number of photons of X-rays corresponding to each of said first predetermined regions in said energy regions is obtained by correcting said preliminary measurement value based on a parameter of said image capturing for medical use.

5. An image capturing system for medical use, comprising:
   a detecting unit for detecting an X-ray dose by absorbing X-rays passed through a subject in image capturing for medical use and outputting absorbed X-ray dose information;
   an obtaining unit for obtaining image information of said subject from said absorbed X-ray dose information;
   an image processing unit for calculating average detection energy in each first predetermined region in said image information, wherein said image processing unit estimates the number of photons of X-rays absorbed by said detecting unit using said image information, to calculate said average detection energy in each said first predetermined region in said image information, and wherein said image processing unit estimates the number of photons of X-rays using average image density information and variance information of image density in each second predetermined region in said image information; and
   an output unit for outputting said average detection energy.

6. An image processing apparatus, comprising:
   an image processing unit for calculating average detection energy in each first predetermined region in image information obtained by image capturing for medical use performed by an image capturing apparatus for medical use by estimating the number of photons of X-rays absorbed by a detecting unit of said image capturing apparatus for medical use from said image information wherein said image information includes a plurality of pieces of image information obtained by performing image capturing for medical use using X-rays in a plurality of energy regions, and said image processing unit estimates the number of photons of X-rays by using said plurality of pieces of image information and applied X-ray dose information as information of dose of X-rays outputted from an X-ray generator; and
   an output unit for outputting said average detection energy.

7. The image processing apparatus according to claim 6, wherein said applied X-ray dose information includes values of representative energies in said energy regions and the number of photons of X-rays corresponding to said first predetermined regions in said energy regions.

8. The image processing apparatus according to claim 7, further comprising a storing unit for storing values of representative energies in said energy regions, wherein a value of representative energy in each of said energy regions is set in advance based on comparison between a first average detection energy and a second average detection energy, said first average detection energy is an average detection energy related to a predetermined substance obtained based on a distribution of the number of photons of X-rays outputted from said X-ray generator, and said second average detection energy is an average detection energy related to said predetermined substance obtained based on the number of photons of X-rays in each of said energy regions and candidate values of representative energies in said energy regions.

9. The image processing apparatus according to claim 7, further comprising a storing unit for storing a preliminary measurement value of the number of photons corresponding to each of said first predetermined regions of X-rays outputted from said X-ray generator which is set for each tube voltage of said X-ray generator, wherein the number of photons of X-rays corresponding to each of said first predetermined regions in said energy regions is obtained by correcting said preliminary measurement value based on a parameter of said image capturing for medical use.

10. An image processing apparatus, comprising:
an image processing unit for calculating average detection energy in each first predetermined region in image information obtained by image capturing for medical use performed by an image capturing apparatus for medical use by estimating the number of photons of X-rays absorbed by a detecting unit of said image capturing apparatus for medical use from said image information wherein said image processing unit estimates the number of photons of X-rays using average image density information and variance information of image density in each second predetermined region in said image information; and
an output unit for outputting said average detection energy.

11. An image processing method comprising:
calculating average detection energy in each first predetermined region in image information obtained by image capturing for medical use performed by an image capturing apparatus for medical use by estimating the number of photons of X-rays absorbed by a detecting unit of said image capturing apparatus for medical use from said image information, wherein said image information includes a plurality of pieces of image information obtained by performing image capturing for medical use using X-rays in a plurality of energy regions, and in said calculating the number of photons of X-rays is estimated by using said plurality of pieces of image information and applied X-ray dose information as information of dose of X-rays outputted from an X-ray generator; and
outputting said average detection energy.

12. The image processing method according to claim 11, wherein said applied X-ray dose information includes values of representative energies in said energy regions and the number of photons of X-rays corresponding to said first predetermined regions in said energy regions.

13. The image processing method according to claim 12, further comprising setting in advance a value of representative energy in each of said energy regions based on comparison between a first average detection energy and a second average detection energy; and storing the value in a storing unit, wherein said first average detection energy is an average detection energy related to a predetermined substance obtained based on a distribution of the number of photons of X-rays outputted from said X-ray generator, and said second average detection energy is an average detection energy related to said predetermined substance obtained based on the number of photons of X-rays in each of said energy regions and candidate values of representative energies in said energy regions.

14. The image processing method according to claim 12, further comprising storing a preliminary measurement value of the number of photons corresponding to each of said first predetermined regions of X-rays outputted from said X-ray generator which is set for each tube voltage of said X-ray generator; and obtaining the number of photons of X-rays corresponding to each of said first predetermined regions in said energy regions by correcting said preliminary measurement value based on a parameter of said image capturing for medical use.

15. An image processing method comprising:
calculating average detection energy in each first predetermined region in image information obtained by image capturing for medical use performed by an image capturing apparatus for medical use by estimating the number of photons of X-rays absorbed by a detecting unit of said image capturing apparatus for medical use from said image information, wherein in said calculating the number of photons of X-rays is estimated by using average image density information and variance information of image density in each second predetermined region in said image information; and
outputting said average detection energy.

* * * * *

UNITED STATES PATENT AND TRADEMARK OFFICE
CERTIFICATE OF CORRECTION

| | | |
|---|---|---|
| PATENT NO. | : 8,054,940 B2 | Page 1 of 1 |
| APPLICATION NO. | : 12/474470 | |
| DATED | : November 8, 2011 | |
| INVENTOR(S) | : Michitaka Honda et al. | |

It is certified that error appears in the above-identified patent and that said Letters Patent is hereby corrected as shown below:

On the Title Page

Left column, item (73), after "Konica Minolta Medical" replace "& Graphics," with --& Graphic,--.

Signed and Sealed this
Sixth Day of March, 2012

David J. Kappos
*Director of the United States Patent and Trademark Office*